(12) United States Patent
Hunt

(10) Patent No.: US 10,300,263 B1
(45) Date of Patent: May 28, 2019

(54) CLOSURE ASSEMBLY FOR A MEDICAL CONNECTOR

(71) Applicant: Timothy Brandon Hunt, Miami, FL (US)

(72) Inventor: Timothy Brandon Hunt, Miami, FL (US)

( * ) Notice: Subject to any disclaimer, the term of this patent is extended or adjusted under 35 U.S.C. 154(b) by 313 days.

(21) Appl. No.: 15/056,503

(22) Filed: Feb. 29, 2016

Related U.S. Application Data

(60) Provisional application No. 62/126,154, filed on Feb. 27, 2015.

(51) Int. Cl.
*A61M 39/10* (2006.01)
*A61M 39/20* (2006.01)

(52) U.S. Cl.
CPC ........ *A61M 39/20* (2013.01); *A61M 39/1011* (2013.01)

(58) Field of Classification Search
CPC .... A61M 39/20; A61M 39/1011; A61M 5/50; A61M 5/5086
See application file for complete search history.

(56) References Cited

U.S. PATENT DOCUMENTS

| | | |
|---|---|---|
| 732,662 A | 6/1903 | Smith |
| 1,678,991 A | 7/1928 | Marschalek |
| 1,970,631 A | 8/1934 | Sherman |
| 2,477,598 A | 8/1949 | Hain |
| 2,739,590 A | 3/1956 | Yochem |
| 2,823,674 A | 2/1958 | Yochem |
| 2,834,346 A | 5/1958 | Adams |
| 2,875,761 A | 3/1959 | Helmer et al. |
| 2,888,015 A | 5/1959 | Hunt |
| 2,952,255 A | 9/1960 | Hein, Jr. |
| 3,122,280 A | 2/1964 | Goda |
| 3,245,567 A | 4/1966 | Knight |
| 3,323,798 A | 6/1967 | Miller |
| 3,364,890 A | 1/1968 | Andersen |
| 3,598,120 A | 8/1971 | Mass |

(Continued)

FOREIGN PATENT DOCUMENTS

| | | |
|---|---|---|
| EP | 0148116 A | 7/1985 |
| WO | WO 2017086607 | 5/2015 |

*Primary Examiner* — Nathan R Price
*Assistant Examiner* — Tasnim Mehjabin Ahmed
(74) *Attorney, Agent, or Firm* — Malloy & Malloy, P.L.

(57) ABSTRACT

A closure assembly structured to be attached in flow restricting relation to a medical connector and removed therefrom utilizing a push-on and twist-off manipulation. The closure assembly comprises a cap having a preferably male flow restricting portion, wherein the cap is operatively disposed in removable, flow restricting attachment to a female medical connector. A plurality of segments collectively define a sidewall of the cap and are individually and collectively movable between an open orientation and a closed orientation relative to at least the flow restricting portion and a medical connector attached thereto. The closed orientation comprises the plurality of segments disposed in covering, retaining relation to the attached medical connector and the open orientation comprises an outward disposition of the plurality of segments and an accessible, exposure of the flow restricting portion. A tamper evident structure may be operatively associated with a housing assembly of the closure assembly.

28 Claims, 8 Drawing Sheets

(56) References Cited

U.S. PATENT DOCUMENTS

| | | | |
|---|---|---|---|
| 3,610,241 | A | 10/1971 | LeMarie |
| 3,700,215 | A | 10/1972 | Hardman et al. |
| 3,706,307 | A | 12/1972 | Hasson |
| 3,712,749 | A | 1/1973 | Roberts |
| 3,747,751 | A | 4/1973 | Miller et al. |
| 3,872,867 | A | 3/1975 | Killinger |
| 3,905,375 | A | 9/1975 | Toyama |
| 3,937,211 | A | 2/1976 | Merten |
| 4,043,334 | A | 8/1977 | Brown et al. |
| 4,046,145 | A | 9/1977 | Choksi et al. |
| 4,216,585 | A | 8/1980 | Hatter |
| 4,216,872 | A | 8/1980 | Bean |
| 4,244,366 | A | 1/1981 | Raines |
| 4,252,122 | A | 2/1981 | Halvorsen |
| 4,286,591 | A | 9/1981 | Raines |
| 4,313,539 | A | 2/1982 | Raines |
| 4,420,085 | A | 12/1983 | Wilson et al. |
| 4,430,077 | A | 2/1984 | Mittleman et al. |
| 4,457,445 | A | 7/1984 | Hanks et al. |
| 4,521,237 | A | 6/1985 | Logothetis |
| 4,530,697 | A | 7/1985 | Kuhlemann et al. |
| 4,571,242 | A | 2/1986 | Klein et al. |
| 4,589,171 | A | 5/1986 | McGill |
| 4,667,837 | A | 5/1987 | Vitello et al. |
| 4,693,707 | A | 9/1987 | Dye |
| 4,726,483 | A | 2/1988 | Drozd |
| 4,743,229 | A | 5/1988 | Chu |
| 4,743,231 | A | 5/1988 | Kay et al. |
| 4,760,847 | A | 8/1988 | Vaillancourt |
| 4,832,695 | A | 5/1989 | Rosenberg et al. |
| 4,834,706 | A | 5/1989 | Beck et al. |
| 4,842,592 | A | 6/1989 | Caggiani et al. |
| 4,844,906 | A | 7/1989 | Hermelin et al. |
| 4,906,231 | A | 3/1990 | Young |
| 4,919,285 | A | 4/1990 | Roof et al. |
| 5,009,323 | A | 4/1991 | Montgomery et al. |
| 5,049,129 | A | 9/1991 | Zdeb et al. |
| 5,057,093 | A | 10/1991 | Clegg et al. |
| 5,135,496 | A | 8/1992 | Vetter et al. |
| 5,165,560 | A | 11/1992 | Ennis, III et al. |
| 5,230,429 | A | 7/1993 | Etheredge, III |
| 5,267,983 | A | 12/1993 | Oilschlager et al. |
| 5,292,308 | A | 3/1994 | Ryan |
| 5,295,599 | A * | 3/1994 | Smith ............... B01L 3/50825 215/204 |
| 5,328,466 | A | 7/1994 | Denmark |
| 5,328,474 | A | 7/1994 | Raines |
| 5,356,380 | A | 10/1994 | Hoekwater et al. |
| 5,380,295 | A | 1/1995 | Vacca |
| 5,405,339 | A | 4/1995 | Kohnen et al. |
| 5,458,580 | A | 10/1995 | Hajishoreh |
| 5,468,224 | A | 11/1995 | Souryal |
| 5,531,695 | A | 7/1996 | Swisher |
| 5,540,666 | A | 7/1996 | Barta et al. |
| 5,549,571 | A | 8/1996 | Sak |
| 5,558,648 | A | 9/1996 | Shields |
| 5,584,817 | A | 12/1996 | van den Haak |
| 5,588,239 | A | 12/1996 | Anderson |
| 5,624,402 | A | 4/1997 | Imbert |
| 5,674,209 | A * | 10/1997 | Yarger ............... A61M 39/20 128/912 |
| 5,700,247 | A | 12/1997 | Grimard et al. |
| 5,702,374 | A | 12/1997 | Johnson |
| 5,776,124 | A | 7/1998 | Wald |
| 5,785,691 | A | 7/1998 | Vetter et al. |
| 5,797,885 | A | 8/1998 | Rubin |
| 5,807,343 | A | 9/1998 | Tucker et al. |
| 5,883,806 | A | 3/1999 | Meador et al. |
| 5,884,457 | A | 3/1999 | Ortiz et al. |
| 5,902,269 | A | 5/1999 | Jentzen |
| 5,951,522 | A | 9/1999 | Rosato et al. |
| 5,951,525 | A | 9/1999 | Thorne et al. |
| 5,954,657 | A | 9/1999 | Rados |
| 5,957,166 | A | 9/1999 | Safabash |
| 5,989,227 | A | 11/1999 | Vetter et al. |
| 6,000,548 | A | 12/1999 | Tsals |
| 6,021,824 | A | 2/2000 | Larsen et al. |
| 6,027,482 | A | 2/2000 | Imbert |
| 6,068,614 | A | 5/2000 | Kimber et al. |
| 6,126,640 | A | 10/2000 | Tucker et al. |
| 6,190,364 | B1 | 2/2001 | Imbert |
| 6,193,688 | B1 | 2/2001 | Balestracci et al. |
| 6,196,593 | B1 | 3/2001 | Petrick et al. |
| 6,196,998 | B1 | 3/2001 | Jansen et al. |
| 6,235,376 | B1 | 5/2001 | Miyazaki et al. |
| 6,280,418 | B1 | 8/2001 | Reinhard et al. |
| 6,287,671 | B1 | 9/2001 | Bright et al. |
| 6,322,543 | B1 | 11/2001 | Singh et al. |
| 6,338,200 | B1 | 1/2002 | Baxa et al. |
| 6,375,640 | B1 | 4/2002 | Teraoka |
| 6,394,983 | B1 | 5/2002 | Mayoral et al. |
| 6,485,460 | B2 | 11/2002 | Eakins et al. |
| 6,500,155 | B2 | 12/2002 | Sasso |
| 6,520,935 | B1 | 2/2003 | Jansen et al. |
| 6,540,697 | B2 | 4/2003 | Chen |
| 6,565,529 | B1 | 5/2003 | Kimber et al. |
| 6,581,792 | B1 | 6/2003 | Limanjaya |
| 6,585,691 | B1 | 7/2003 | Vitello |
| 6,592,251 | B2 | 7/2003 | Edwards et al. |
| 6,682,798 | B1 | 1/2004 | Kiraly |
| 6,726,652 | B2 | 4/2004 | Eakins et al. |
| 6,726,672 | B1 | 4/2004 | Hanley et al. |
| 6,755,220 | B2 | 6/2004 | Castellano et al. |
| 6,764,469 | B2 | 7/2004 | Broselow |
| 6,821,268 | B2 | 11/2004 | Balestracci |
| 6,921,383 | B2 | 7/2005 | Vitello |
| 6,942,643 | B2 | 9/2005 | Eakins et al. |
| 7,055,273 | B2 | 6/2006 | Roshkoff |
| 7,141,286 | B1 | 11/2006 | Kessler et al. |
| 7,182,256 | B2 | 2/2007 | Andreasson et al. |
| 7,240,926 | B2 | 7/2007 | Dalle et al. |
| 7,374,555 | B2 | 5/2008 | Heinz et al. |
| 7,404,500 | B2 | 7/2008 | Marteau et al. |
| 7,410,803 | B2 | 8/2008 | Nollert et al. |
| 7,425,208 | B1 | 9/2008 | Vitello |
| 7,437,972 | B2 | 10/2008 | Yeager |
| 7,482,166 | B2 | 1/2009 | Nollert et al. |
| 7,588,563 | B2 | 9/2009 | Guala |
| 7,594,681 | B2 | 9/2009 | DeCarlo |
| 7,632,244 | B2 | 12/2009 | Buehler et al. |
| 7,641,636 | B2 | 1/2010 | Moesli et al. |
| 7,735,664 | B1 | 6/2010 | Peters et al. |
| 7,748,892 | B2 | 7/2010 | McCoy |
| 7,762,988 | B1 | 7/2010 | Vitello |
| 7,766,919 | B2 | 8/2010 | Delmotte |
| 7,802,313 | B2 | 9/2010 | Czajka |
| 7,918,830 | B2 | 4/2011 | Langan et al. |
| 8,079,518 | B2 | 12/2011 | Turner et al. |
| 8,091,727 | B2 | 1/2012 | Domkowski |
| 8,137,324 | B2 | 3/2012 | Bobst |
| 8,140,349 | B2 | 3/2012 | Hanson et al. |
| 8,257,286 | B2 | 9/2012 | Meyer et al. |
| 8,328,082 | B1 | 12/2012 | Bochenko et al. |
| 8,348,895 | B1 | 1/2013 | Vitello |
| 8,353,869 | B2 | 1/2013 | Ranalletta et al. |
| 8,443,999 | B1 | 5/2013 | Reinders |
| D684,057 | S | 6/2013 | Kwon |
| 8,512,277 | B2 | 8/2013 | Del Vecchio |
| 8,556,074 | B2 | 10/2013 | Turner et al. |
| 8,579,116 | B2 | 11/2013 | Pether et al. |
| 8,591,462 | B1 | 11/2013 | Vitello |
| 8,597,255 | B2 | 12/2013 | Emmott et al. |
| 8,597,271 | B2 | 12/2013 | Langan et al. |
| 8,616,413 | B2 | 12/2013 | Koyama |
| D701,304 | S | 3/2014 | Lair et al. |
| 8,672,902 | B2 | 3/2014 | Ruan et al. |
| 8,702,674 | B2 | 4/2014 | Bochenko |
| 8,777,930 | B2 | 7/2014 | Swisher et al. |
| 8,852,561 | B2 | 10/2014 | Wagner et al. |
| 8,864,021 | B1 | 10/2014 | Vitello |
| 8,864,707 | B1 | 10/2014 | Vitello |
| 8,864,708 | B1 | 10/2014 | Vitello |
| 8,945,082 | B2 | 2/2015 | Geiger et al. |
| 9,101,534 | B2 | 8/2015 | Bochenko |

(56) References Cited

U.S. PATENT DOCUMENTS

| | | |
|---|---|---|
| 9,199,042 B2 | 12/2015 | Farrar et al. |
| 9,199,749 B1 | 12/2015 | Vitello |
| 9,220,486 B2 | 12/2015 | Schweiss et al. |
| 9,220,577 B2 | 12/2015 | Jessop et al. |
| 9,272,099 B2 | 3/2016 | Limaye et al. |
| 9,311,592 B1 | 4/2016 | Vitello |
| D756,777 S | 5/2016 | Berge et al. |
| 9,336,669 B2 | 5/2016 | Bowden et al. |
| D759,486 S | 6/2016 | Ingram et al. |
| 9,402,967 B1 | 8/2016 | Vitello |
| 9,427,715 B2 | 8/2016 | Palazzolo et al. |
| 9,433,768 B2 | 9/2016 | Tekeste et al. |
| 9,463,310 B1 | 10/2016 | Vitello |
| D773,043 S | 11/2016 | Insgram et al. |
| D789,529 S | 6/2017 | Davis et al. |
| 9,687,249 B2 | 6/2017 | Hanlon et al. |
| D797,928 S | 9/2017 | Davis et al. |
| D797,929 S | 9/2017 | Davis et al. |
| 9,855,191 B1 | 1/2018 | Vitello |
| D815,945 S | 4/2018 | Fischer et al. |
| D825,746 S | 8/2018 | Davis et al. |
| 2001/0034506 A1 | 10/2001 | Hirschman et al. |
| 2001/0056258 A1 | 12/2001 | Evans |
| 2002/0023409 A1 | 2/2002 | Py |
| 2002/0097396 A1 | 7/2002 | Schafer |
| 2002/0099334 A1 | 7/2002 | Hanson et al. |
| 2002/0101656 A1 | 8/2002 | Blumenthal et al. |
| 2002/0133119 A1 | 9/2002 | Eakins et al. |
| 2003/0146617 A1 | 8/2003 | Franko, Sr. |
| 2003/0183547 A1 | 10/2003 | Heyman |
| 2004/0064095 A1 | 4/2004 | Vitello |
| 2004/0116858 A1 | 6/2004 | Heinz et al. |
| 2004/0186437 A1 | 9/2004 | Frenette et al. |
| 2004/0225258 A1 | 11/2004 | Balestracci |
| 2005/0146081 A1 | 7/2005 | MacLean et al. |
| 2005/0148941 A1 | 7/2005 | Farrar et al. |
| 2005/0209555 A1 | 9/2005 | Middleton et al. |
| 2006/0084925 A1 | 4/2006 | Ramsahoye |
| 2006/0089601 A1 | 4/2006 | Dionigi |
| 2006/0173415 A1 | 8/2006 | Cummins |
| 2006/0189933 A1 | 8/2006 | Alheidt |
| 2007/0060898 A1 | 3/2007 | Shaughnessy et al. |
| 2007/0106234 A1 | 5/2007 | Klein |
| 2007/0142786 A1 | 6/2007 | Lampropoulos et al. |
| 2007/0191690 A1 | 8/2007 | Hasse |
| 2007/0219503 A1 | 9/2007 | Loop |
| 2007/0257111 A1 | 11/2007 | Ortenzi |
| 2008/0068178 A1 | 3/2008 | Meyer |
| 2008/0097310 A1 | 4/2008 | Buehler et al. |
| 2008/0106388 A1 | 5/2008 | Knight |
| 2008/0243088 A1 | 10/2008 | Evans |
| 2008/0306443 A1 | 12/2008 | Neer |
| 2009/0099552 A1 | 4/2009 | Levy et al. |
| 2009/0149815 A1 | 6/2009 | Kiel et al. |
| 2009/0326481 A1 | 12/2009 | Swisher et al. |
| 2010/0084403 A1 | 4/2010 | Popish et al. |
| 2010/0126894 A1 | 5/2010 | Koukol et al. |
| 2010/0179822 A1 | 7/2010 | Reppas |
| 2010/0228226 A1 | 9/2010 | Nielsen |
| 2010/0252564 A1 | 10/2010 | Martinez et al. |
| 2010/0283238 A1 | 11/2010 | Deighan et al. |
| 2011/0044850 A1 | 2/2011 | Solomon et al. |
| 2011/0046550 A1 | 2/2011 | Schiller et al. |
| 2011/0046603 A1 | 2/2011 | Felsovalyi et al. |
| 2012/0064515 A2 | 3/2012 | Knapp et al. |
| 2012/0096957 A1 | 4/2012 | Ochman |
| 2012/0110950 A1 | 5/2012 | Schraudolph |
| 2013/0018356 A1 | 1/2013 | Prince et al. |
| 2013/0088354 A1 | 4/2013 | Thomas |
| 2013/0237949 A1 | 9/2013 | Miller |
| 2014/0000781 A1 | 1/2014 | Franko, Jr. |
| 2014/0034536 A1 | 2/2014 | Reinhardt et al. |
| 2014/0069829 A1 | 3/2014 | Evans |
| 2014/0135738 A1* | 5/2014 | Panian ............... A61M 39/20 604/535 |
| 2014/0155868 A1 | 6/2014 | Nelson et al. |
| 2014/0257843 A1 | 9/2014 | Adler et al. |
| 2014/0326727 A1 | 11/2014 | Jouin |
| 2014/0353196 A1 | 12/2014 | Key |
| 2015/0191633 A1 | 7/2015 | De Boer et al. |
| 2015/0305982 A1 | 10/2015 | Bochenko |
| 2015/0310771 A1 | 10/2015 | Atkinson et al. |
| 2016/0067422 A1 | 3/2016 | Davis et al. |
| 2016/0090456 A1 | 3/2016 | Ishimaru |
| 2016/0144119 A1 | 5/2016 | Limaye et al. |
| 2016/0158110 A1 | 6/2016 | Swisher et al. |
| 2016/0158449 A1 | 6/2016 | Limaye et al. |
| 2016/0176550 A1 | 6/2016 | Vitello et al. |
| 2016/0328586 A1 | 11/2016 | Bowden et al. |
| 2016/0361235 A1 | 12/2016 | Swisher |
| 2016/0367439 A1 | 12/2016 | Davis et al. |
| 2017/0014310 A1 | 1/2017 | Hyun et al. |
| 2017/0124289 A1 | 5/2017 | Hasan |
| 2017/0173321 A1 | 6/2017 | Davis et al. |
| 2017/0203086 A1 | 7/2017 | Davis |
| 2017/0319438 A1 | 11/2017 | Davis et al. |
| 2018/0001540 A1 | 1/2018 | Byun |
| 2018/0089593 A1 | 3/2018 | Patel et al. |

* cited by examiner

CLOSURE ASSEMBLY FOR A MEDICAL CONNECTOR

CLAIM OF PRIORITY

The present application is based on and a claim of priority is made under 35 U.S.C. Section 119(e) to a provisional patent application that is in the U.S. Patent and Trademark Office, namely, that having Ser. No. 62/126,154 and a filing date of Feb. 27, 2015 and which is incorporated herein by reference.

BACKGROUND OF THE INVENTION

Field of the Invention

This invention is directed to a closure assembly, which may be operative in a "push-on, twist-off" mode, and which is structured to be attached in flow-restricting relation to a medical connector. The invention includes a closure cap having a flow-restricting portion and a sidewall defined by a plurality of segments positionable between open and closed orientations, relative to the flow-restricting portion and the medical connector attached thereto. A housing assembly may be disposed in enclosing, retaining relation to the closure cap and may include a tamper evident structure.

Description of the Related Art

In the medical field, it is a relatively common procedure to administer fluids to patients using syringes, intravenous (IV) infusion devices, medical tubing, etc. Such devices or assemblies are useful in the treatment of a number of medical conditions, in that a variety of fluids and/or medicines can be administered to a patient utilizing such assemblies over a prescribed period of time and in controlled amounts. By way of example, a conventional IV administration assembly typically includes a reservoir or container, in the form of a bottle or more commonly, a flexible material bag, suspended on a pole or a like support structure located substantially adjacent to the patient being treated, typically in an elevated relation thereto. In addition, the IV fluid flows from the supported and elevated IV bag to the patient by means of elongated, flexible medical tubing connected at a proximal end to the IV bag and at the other distal end, connected intravenously to the patient by way of a catheter or like structure. The IV delivery tube is also structured to connect at one end or to be interconnected with an appropriate connector, often having somewhat of a "Y" shape, that is associated with the IV assembly and in fluid communication with either the contents of the IV bag or alternatively, with the catheter in use on the patient for intravenous administration of fluids and medicines.

One such connector may be in the form of a female connector attached to the IV bag or other container and disposed in fluid communication with the contents thereof. An appropriate female connector may be, but is not limited to, a female luer connector which at least partially defines, along with a male luer connector, a "luer lock" connector assembly, as is well known in the medical profession. The male connector is secured to the IV delivery tubing, such as at the proximal end, and is specifically structured to be attached to the female connector in a manner which establishes fluid communication with contents of the IV container, and facilitates a flow of the IV fluid from the IV container through the connected male and female connectors. As a result, fluid flow between the patient and the interior of the IV bag is established. As is also well known, various types of valves and/or flow regulating devices may be operatively associated with the IV assembly to regulate the amount of fluid or rate of fluid delivery to the patient during the administration procedure.

In addition, known IV containers or reservoirs may incorporate an additional female luer connector, or other female type connector, disposed in fluid communication with the IV delivery tubing, such as but not limited to at the IV bag. This additional female connector is provided to administer additional liquid agents, such as pain medication, antibiotics, and/or other medicinal compositions, to the IV fluid being delivered to the patient. However, such an additional female connector may remain unused or may be accessed subsequently to the initiation of the IV fluid administration, such as when additional medication or another composition is required or prescribed.

In periods of non-use, it is important to maintain a female connector in a closed and fluid sealed condition in order to maintain sterility, and also, the integrity of the IV fluid prior to use. This is also important in order to restrict unauthorized access to the IV fluid and even to the female connector.

Therefore, there is a need in the medical field for an efficient, effective and easily applied closure assembly that would be capable of closing and sealing a female connector during periods of its non-use. Moreover, if any such closure assembly were developed, it would preferably also be structured for efficient attachment to the female connector in a manner which restricts or perhaps even stops fluid flow from the female connector and potentially also a fluid reservoir to which it is attached. In addition, if any such closure assembly were developed it would also preferably be structured to provide a clear indication whenever there has been tampering or other attempted access to the female connector and/or contents of the IV container or other fluid reservoir associated with the female connector. Additionally, if any such closure assembly were developed, it would also ideally be capable of being removed from the female connector in a manner which provides an appropriate indication of complete, partial or other attempted access to the female connector. Finally, the structural components as well as the operational characteristics of any such closure assembly developed should ideally also provide a sufficient degree of reliability relating to the secure closing and sealing of the female connector to which it is attached, while restricting access and clearly indicating when access thereto has occurred or been attempted.

Yet additional features which would preferably be included in any such closure assembly, especially for a female medical connector, may be the ability to facilitate its attachment and detachment therefrom such as, but not limited to being attached and removed in a "push-on, twist-off" manner.

SUMMARY OF THE INVENTION

The present invention is intended to solve these and other problems that remain in this field of art, and as such, is directed to a closure assembly structured to be operatively attached in flow restricting relation to a "medical connector" or like device. As described in greater detail hereinafter, the structural and operational versatility of the various embodiments of the closure assembly facilitate its flow restricting attachment on needleless syringes, IV assemblies, connectors, medical tubing, other closures, etc. having different structural configurations.

By way of example only, the "medical connector" to which the closure assembly may be attached may include, but should not be limited to, a lure connector, an enteral connector, neuraxial connector as well as other connector type structures utilized in the medical and related arts. Moreover, one or more preferred embodiments of the closure assembly of the present invention may be operative in a "push-on, twist-off" mode for respective attachment to and removal from a female connector, as will also be explained in greater detail hereinafter.

More specifically, at least one preferred embodiment of the closure assembly of the present invention includes a closure cap including a base and a flow restricting portion preferably connected to the base and disposed on an interior of the closure cap. Further, such flow restricting portion may be in the form of a plug projecting outwardly from the base in receiving relation to a fluid flow port of a female connector. In addition, the closure cap includes at least one but preferably a plurality of segments which collectively define a sidewall of the closure cap. Moreover, each of the one or more segments are movably and more specifically hingedly attached, such as by a "living hinge", to the base and movable relative thereto. In more specific terms, the one or more segments are independently and/or collectively movable into and between an open orientation and a closed orientation. As such, each of the one or more segments is movable relative to the flow restricting portion, a medical connector attached thereto and/or the interior of the cap. Further, the aforementioned "living hinge" may be integrally formed in interconnecting relation between the base and respective ones of the segments.

In the open orientation, the one or more segments extend outwardly away from the interior and base of the cap and flow restricting portion. In contrast, the closed orientation comprises the one or more segments disposed inwardly, towards the flow restricting portion of the cap in enclosing, covering and retaining relation with exterior portions of the medical connector to which the closure cap is attached. Accordingly, in the open orientation the flow restricting portion or male plug of the cap is readily exposed thereby facilitating a "push-on" manipulation of a female medical connector onto the male plug or other male type flow restricting member.

In contrast, when in the closed orientation, internal surface portions of the one or more segments are disposed and structured to establish and maintain a retaining engagement with exterior, correspondingly disposed portions of the medical connector. The closed orientation can be more specifically defined, in one or more embodiments, by interior surface portions of the one or more segments being cooperatively structured with exterior portions of the medical connector to define the retaining engagement there between as a "mating engagement", which in turn, may be defined by a threaded engagement, between the interior surfaces of the one or more segments and the correspondingly disposed, exterior surface of the medical connector.

Additional structural and operative features of the closure assembly include a housing assembly. In at least one embodiment, the housing assembly comprises a closure sleeve having an access opening formed at one end thereof. The closure sleeve and the access opening are cooperatively dimensioned with the exterior of the closure cap to facilitate its passage into the interior of the closure sleeve. Moreover, when initially in the open orientation and with the medical connector being attached thereto, the closure cap may be forced into the access opening and pass into the interior of the closure sleeve. In doing so, the cooperative dimensioning of the access opening will allow passage of the closure cap there through but concurrently force the one or more segments from the open orientation into the closed orientation. As set forth above, when in the closed orientation the interior surfaces of the one or more segments will be forced into mating engagement with exterior portions or surfaces of the medical connector. It is further noted that in at least one embodiment, once disposed on the interior of the closure sleeve, the closure cap and the medical connector attached thereto, may freely rotate within the closure cap in opposite directions.

Yet additional structural features of one or more embodiments of the closure assembly include the provision of a retention structure formed on interior portions of the closure sleeve. Such a retention structure includes an inwardly protruding wall portion which may be disposed in interruptive, abutting relation to an exterior portion of the closure cap. Therefore, any attempt to remove the medical connector and attached closure cap, such as by exerting an outwardly directed pulling force thereon, will result in abutting, retaining engagement of the retention structure on the interior of the closure cap and the corresponding protruding portion on the exterior surface of the closure cap. This abutting interaction will prevent the closure cap and the attached medical connector from being "pulled" from the interior of the closure sleeve.

In addition, due to the free rotation of the closure cap within the interior of the closure sleeve, the medical connector will normally not be able to be "unthreaded" or rotated relative to the closure cap. Therefore, removal of the medical connector from the closure cap, while on the interior of the closure sleeve, may be accomplished by exerting an inwardly, oppositely directed "squeezing" force on the exterior of the closure sleeve. This squeezing force will serve to "pinch" or capture the closure cap in a fixed position on the interior of the closure sleeve. As a result, the medical connector will be able to be unthreaded, rotated or "twisted" out of its flow restricting attachment with the closure cap and detachment from the male plug or flow restricting portion.

In yet one or more additional preferred embodiments, the requirement of exerting the aforementioned "squeezing" force on the exterior of the closure sleeve in order to remove the medical connector from the closure cap is eliminated. This is accomplished through the provision of a positive coupling between the closure sleeve and the closure cap. Such a positive coupling may be in the form of a "ramp and cliff" type connector attached to corresponding, interactive portions on the interior of the closure sleeve and the exterior of the closure cap. Such a positive coupling or "ramp and cliff" type connector will allow a fixed positioning of the closure cap on the interior of the closure sleeve in at least one direction, while the medical connector is being unthreaded or twisted from the flow restricting attachment and the closure cap.

In one or more additional preferred embodiments, a positive coupling structure may be disposed within the closure sleeve and be mounted in part on both the closure sleeve and a corresponding portion of the closure cap. Such a positive coupling may be in the form of a "cliff and ramp" type structure or other or other coupling. In operation, the positive coupling facilitates free rotation of the closure cap relative to the closure sleeve in one direction. However, in the opposite direction the positive coupling will engage and at least temporarily fix the closure cap to the closure sleeve, thereby allowing removal of the medical connector from the closure cap by the medical connector being unthreaded, rotated or twisted there from. Further, the inclusion of the positive coupling, as set forth above, will eliminate the need for the "squeezing" force being exerted on the exterior of the closure sleeve in order to facilitate the unthreading or twist-off of the medical connector from the closure cap.

Yet an additional feature of one or more other embodiments of the closure assembly comprises a tamper evident structure operative to clearly indicate an attempted or actual access to the medical connector and/or its contents. More specifically, the housing assembly may include an outer cover disposed in surrounding, enclosing relation to the closure sleeve and the closure cap, when disposed within the interior of the closure sleeve. Further, this tamper evident embodiment includes a tamper evident structure preferably, but not exclusively, in the form of a ring or like structure removably connected to the exterior surface thereof. As such, the outer cover of the housing assembly includes interior structural portions disposed in interruptive, abutting engagement with the tamper evident ring or other type structure. Accordingly when a sufficient, outwardly directed pulling force is exerted on the medical connector, the tamper evident ring or like structure will be forced into abutting engagement with the interior structure of the outer cover. This will result in disconnection of the ring from the exterior surface of the closure sleeve and a capturing of the ring inside the outer cover. Therefore, a disconnection of the tamper evident structure will be indicative of an intended or actual use and/or access to the medical connector and/or the contents of a fluid reservoir associated with the medical connector.

Therefore, the one or more preferred embodiments of the closure assembly of the present invention represents an efficient and easy-to-use, "push-on, twist-off" structure for establishing a flow restricting or even flow stopping attachment with one of a possible variety of medical connectors such as, but not limited to, those set forth herein.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the Detailed Description of the Invention(s) set forth below, as taken in connection with the accompanying drawings in which.

Like reference numerals refer to like parts throughout the several views of the drawings.

DETAILED DESCRIPTION OF THE INVENTION IN ILLUSTRATED EMBODIMENTS

As represented in the accompanying Figures, the present invention is directed to a closure assembly, generally indicated throughout the Figures as 10, which is structured for flow restricting relation, and in some cases flow stopping relation, to a medical connector, generally indicated as 12. By way of example only, the "medical connector" 12 to which the closure assembly 10 may be attached may include, but not be limited to, a lure connector, Enteral connector, Neuraxial connector, as well as other connector type structures including a needleless syringe, IV assembly, medical tubing, etc., commonly utilized in the medical and related arts. Moreover, one or more preferred embodiments of the closure assembly 10 may be operative in a "push-on, twist-off" mode for respective attachment to and removal from a female type medical connector 12, as will also be explained in greater detail hereinafter.

Figure 2:
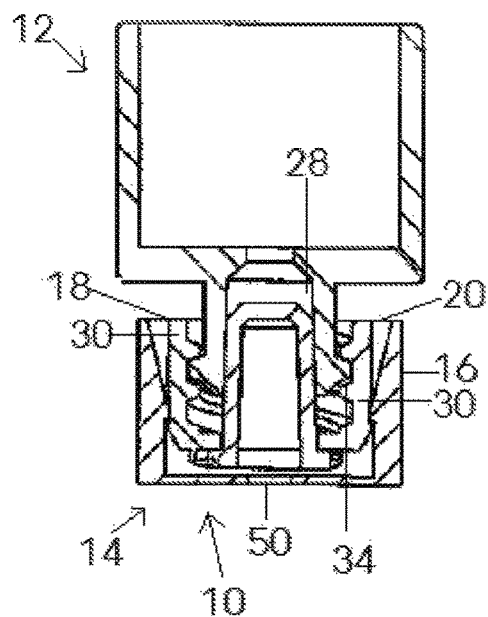
FIG. 2 is a sectional view taken along line 2-2 of FIG. 1.
Figure 3:
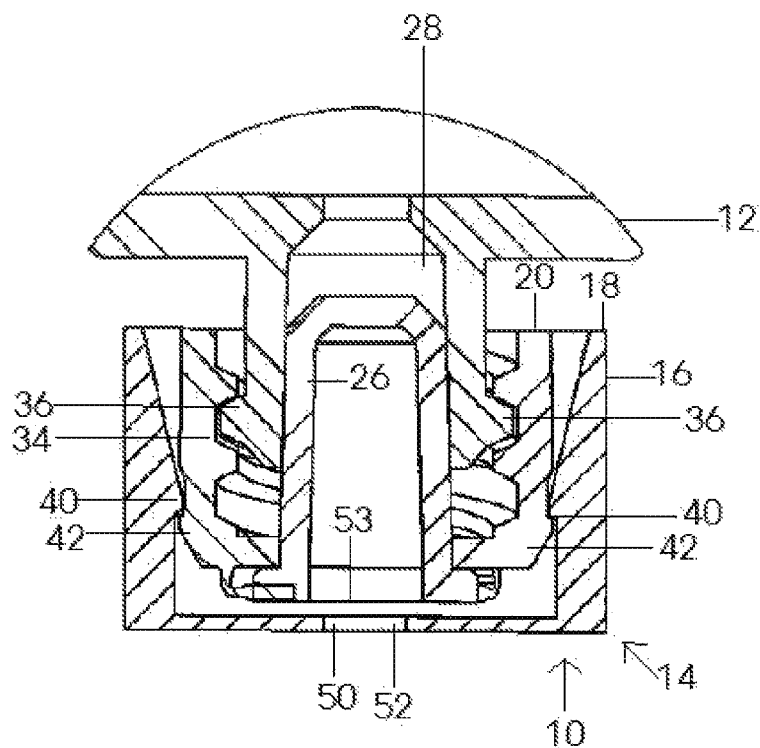
FIG. 3 is a detailed sectional view of interior portions of the closure assembly illustrated in FIGS. 1 and 2 and operatively attached in flow restricting relation to a medical connector.

With initial reference to FIGS. 2 and 3, the closure assembly 10 also includes a housing assembly, generally indicated as 14, and further, includes at least a closure sleeve 16. The closure sleeve 16 includes an open end or access opening 18 in which a closure cap 20 may be operatively disposed, such as when it is connected in flow restricting relation to the medical connector 12.

Figure 4:
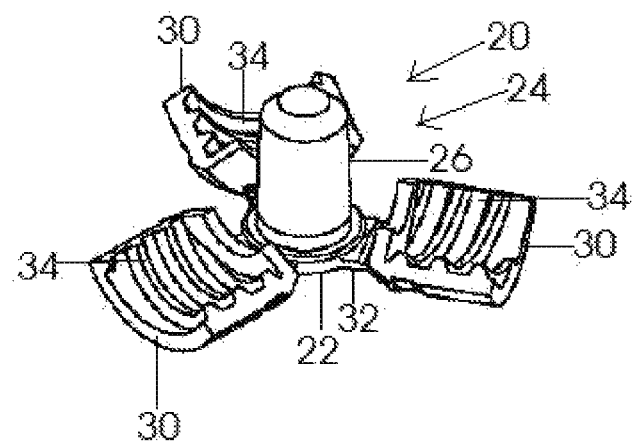
FIG. 4 is a perspective view of the un-attached closure cap of the embodiments of FIGS. 1-3 in an open orientation.

With primary reference now to FIGS. 3 and 4, the invention is shown to include a closure cap 20 having a base 22 and a flow restricting portion generally indicated as 24. In one or more preferred embodiments of the closure assembly 10, the flow restricting portion 24 preferably includes a male plug 26 designed to be inserted in flow restricting or even in flow stopping relation to a female port 28 shown in FIGS. 2 and 3 (or which may be referred to herein as a female fluid flow port 28) when the connector 12 is operatively attached to the closure cap 20.

As is perhaps best shown in FIG. 4 and FIGS. 5A-5D, additional structural and operative features of the closure cap 20 include at least one, but preferably, a plurality of segments 30, each movably connected to the base 22. In more specific terms, each of the one or more segments 30 may be hingedly connected to the base 22 and/or other appropriate portions of the closure cap 20 by a "living hinge" as indicated at 32. Further, each of the one or more segments 30 are independently and collectively movable between an open orientation as represented in FIG. 4 and a closed orientation as represented in FIGS. 2-3. It is noted that the number of segments 30 may vary, and depending upon the number actually included in the cap 20, the plurality of segments may collectively, at least partially or completely, define the sidewall of the cap 20, as should be evident when the plurality of segments 30 are in the closed orientation of FIGS. 2-3.

Figure 5A:
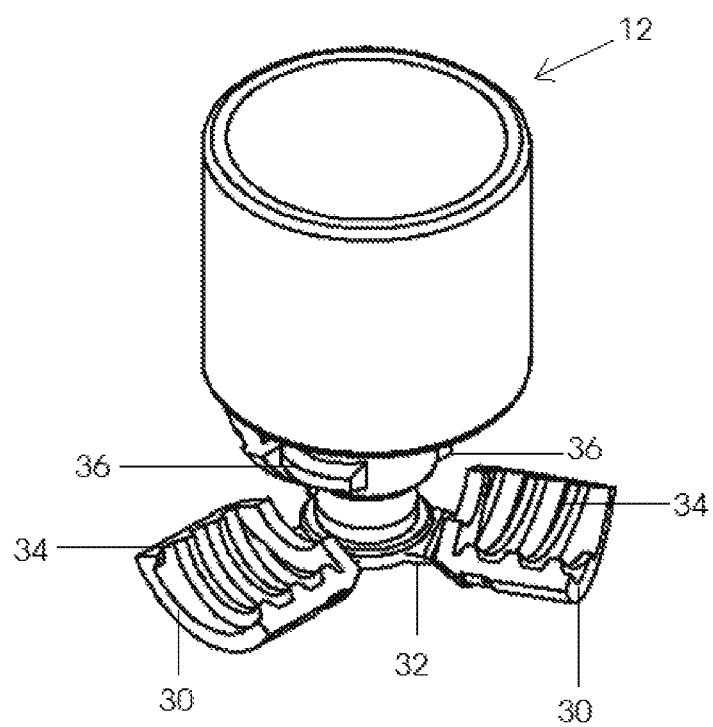
FIGS. 5A-5D are successive perspective views representing the progressive steps of attaching the closure cap and a remainder of the closure assembly to the medical connector.
Figure 5B:
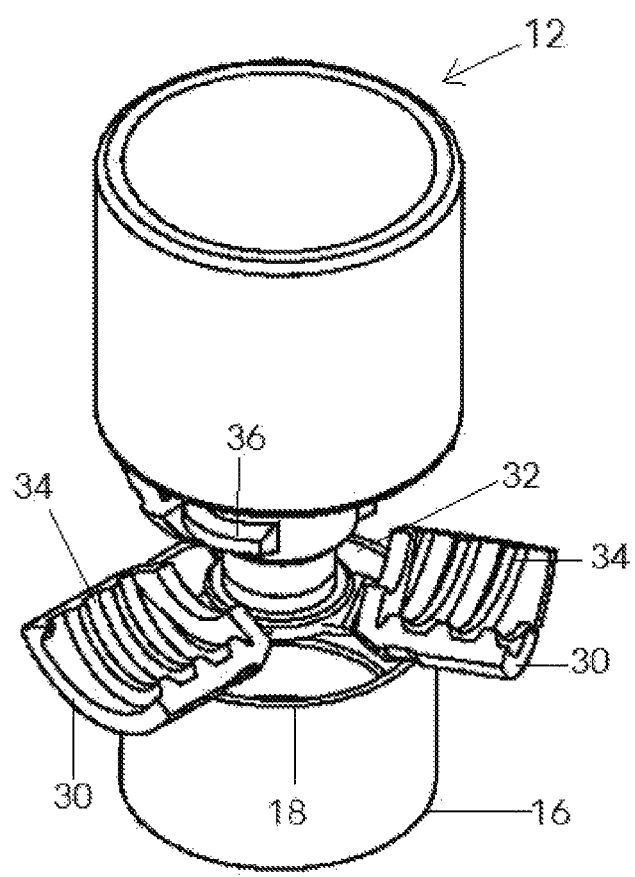

Still referring primarily to FIGS. 4 and 5A-5D, yet additional structural features include the interior surfaces 34 of each of the one or more segments 30 being formed for positioning in a retaining relation to correspondingly disposed exterior portions 36, of the medical connector 12 as shown also in FIGS. 3 and 5A. More specifically, the interior surface 34 of each of the plurality of segments 30 may have a threaded construction corresponding to a threaded exterior portion 36 to form a mating engagement there-between, when the plurality of segments 30 are in the closed orientation of FIGS. 2 and 3. Therefore, the cooperative structuring between the interior surfaces 34 of the plurality of segments 30 and the exterior surface 36 of the medical connector 12 facilitates a retaining, mating engagement between the closure cap 20 and the medical connector 12, when the cap 20 is in the closed orientation and the medical connector 12 is attached in flow restricting relation thereto.

Further, as explained in greater detail hereinafter, these interactive surface portions 34 and 36 may facilitate an unthreading and/or "twist-off" manipulation of the medical connector 12 under certain conditions. Also, and as clearly represented in FIG. 4, when the plurality of segments 30 are in the open orientation, the flow restricting portion 24 in the form of the male plug 26 is readily exposed, thereby facilitating a "push-on" manipulation of the medical connector 12, as will now be explained in further detail with specific reference to FIGS. 5A-5D.

Figure 5C:
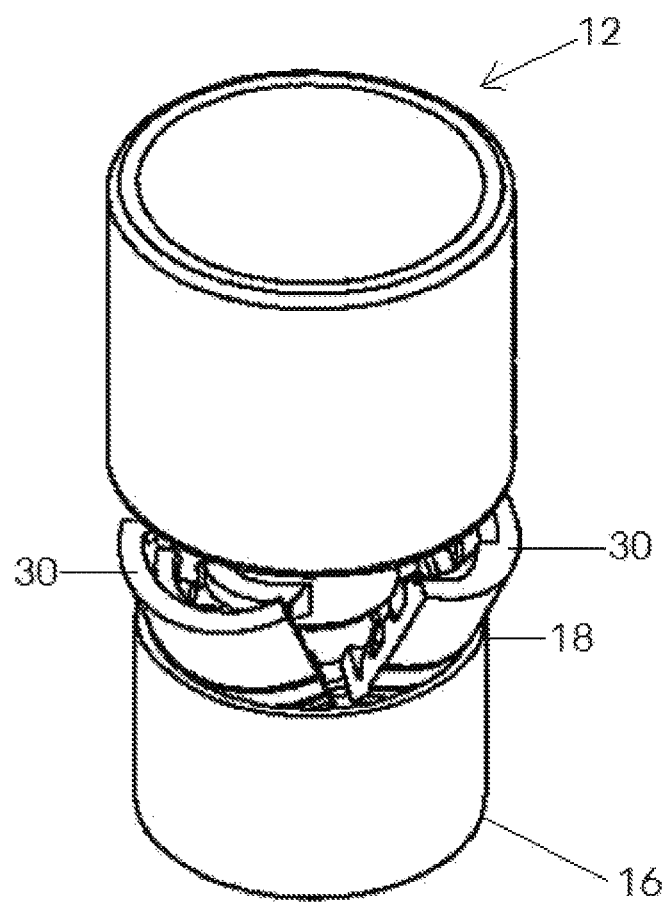
Figure 5D:
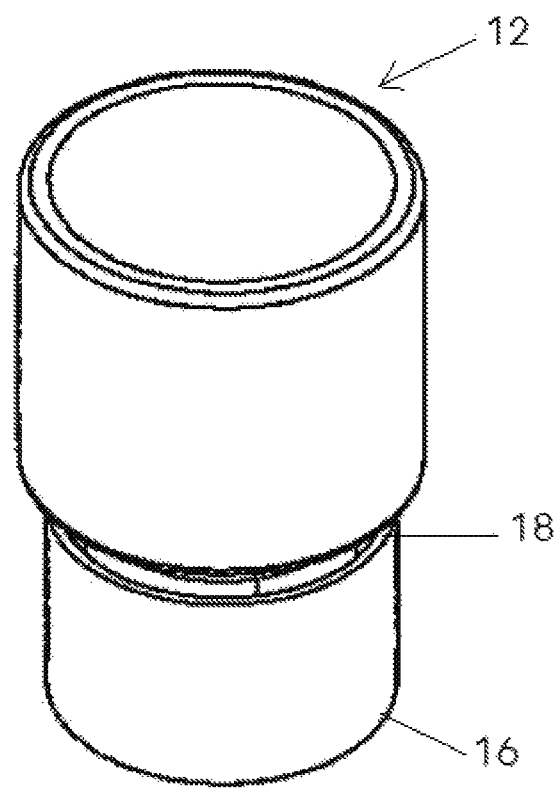

As indicated, FIGS. 5A-5D schematically represent progressive steps in the attachment of the medical connector 12 to the closure cap 20 and the subsequent positioning of the attached cap 20 and medical connector 12 into the interior of the closure sleeve 16 of the housing assembly 14. Accordingly, the medical connector 12 is "pushed-on" the male flow restricting plug 26 and the closure cap 20 is thereby attached in flow restricting relation to the medical connector 12. As represented, the plurality of segments 30 initially remain in the open orientation as represented in FIG. 5A. However, once attached, the combined medical connector 12 and the closure cap 20 are forced through the access opening 18 of the closure sleeve 16, as best represented in FIG. 5C. The exterior and/or circumferential dimension of the closure cap 20, once in the closed orientation, appropriately corresponds with the dimension of the access opening 18 and the hollow interior of the closure sleeve 16. Therefore, forced passage of the attached medical connector 12 and closure cap 20 through the access opening 18 will concurrently force movement of the plurality of segments 30 from the initially open orientation into the closed orientation. Further, as represented in FIGS. 3 and 5D, when in its operative position within the interior of the closure sleeve 16 of the housing assembly 14, the interior surface portions 34 of each or at least some of the plurality of segments 30 are disposed in the aforementioned retaining relation and/or mating, at least partially threaded engagement with the exterior portions 36 of the medical connector 12.

With reference now to FIG. 3, the housing assembly 14 in an embodiment that preferably includes the closure sleeve 16, may also include a retention structure 40 that preferably, but not exclusively, is formed on or is an integral part of the interior wall portion of the closure sleeve 16, as represented. This retention structure 40 extends inwardly into the interior of the closure sleeve 16 into interruptive, abutting and retaining engagement with an outwardly protruding portion 42 on the exterior of the closure cap 20. As a result of this retention structure 40 and its interaction with wall portion 42 of the closure cap 20, removal of the closure cap 20 from the interior of the closure sleeve 16 and/or housing 14 will be resisted and/or prevented.

Figure 1:
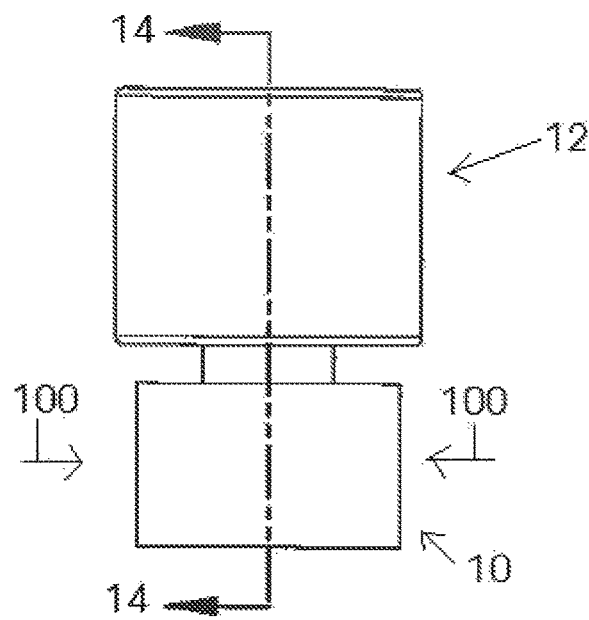
FIG. 1 is a front elevational view of a closure assembly according to the present invention illustrated as being operatively attached in flow restricting relation to a medical connector.

It is further noted that the exterior dimensions of the closure cap 20 and the interior dimensions of the closure sleeve 16 are such as to provide for an unopposed or free rotation of the closure cap 20, in opposite directions, within the interior of the closure sleeve 16. As a result, the medical connector 12 cannot be rotated relative to the closure cap 20 and therefore, cannot be normally removed such as by being unthreaded or untwisted from the closure cap 20. Therefore, removal of the medical connector 12 from the closure cap 20 can be accomplished by the exertion of substantially opposing "squeezing" forces 100 on the exterior of the closure sleeve 16, as schematically represented in FIG. 1. Such a squeezing force 100 will serve to at least temporarily fix the closure cap 20 on the interior of the closure sleeve 16, thereby allowing an unthreading, rotation or twisting of the medical connector 12 from the closure cap 20, facilitating its removal from the male plug 26 of the flow restricting portion 24 and the interior of the cap 20.

Also and as represented in FIGS. 2 and 3, additional structural and operative features which may be included in one or more embodiments of the closure assembly 10 include the provision of a "positive coupling" structure 50 between the closure sleeve 16 and the cap 20, on the interior of the closure sleeve 16. Such a positive coupling 50 is schematically represented and may be in the form of a "ramp and cliff" type connector attached to corresponding, interactive portions, generally indicated as 52 and 53 respectively, on the interior of the closure sleeve 16 and the exterior of the closure cap 20. Such a positive coupling structure or "ramp and cliff" type connector 50 will allow a fixed positioning of the closure cap 20 on the interior of the closure sleeve 16 when the cap is rotated in one predetermined direction. In turn, the medical connector 12 will be allowed to rotate relative to the closure top 20 and be unthreaded or twisted from the flow restricting attachment 24 and the closure cap 20.

As indicated, the positive coupling structure 50 may be disposed within the closure sleeve 16 and be mounted in part on both the closure sleeve 16, as at 52, and a corresponding portion of the closure cap 20, as at 53. In operation, the positive coupling 50 facilitates free rotation of the closure cap 20 relative to the closure sleeve 16 in one direction only. However, attempted rotation in the opposite direction will result in the positive coupling 50 at least temporarily fixing the closure cap 20 to the closure sleeve 16. This temporary fixed positioning of the closure cap 20 allows removal of the medical connector 12 from the closure cap 20 by allowing the medical connector 12 to be rotated, unthreaded or twisted-off off of the male flow restricting plug and the remainder of the closure cap 20. Further, the inclusion of the positive coupling 50, as set forth above, will eliminate the need for the "squeezing" force 100 being exerted on the exterior of the closure sleeve 16 in order to facilitate the temporarily fixed positioning of the closure cap 20 relative to and within the closure sleeve 16 and the unthreading or twist-off of the medical connector 12 from the closure cap 20.

Figure 6:
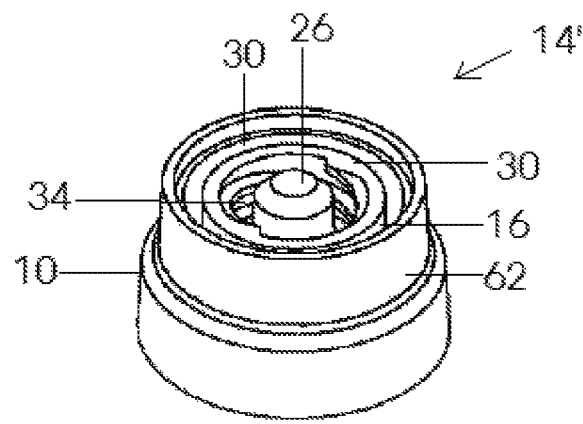
FIG. 6 is a perspective view of an exterior of a closure assembly in accordance with the present invention in another embodiment including a tamper evident structure.
Figure 7:
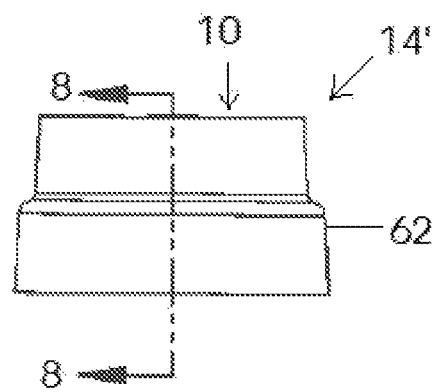
FIG. 7 is a front elevational view of the embodiment illustrated in FIG. 6.
Figure 8:
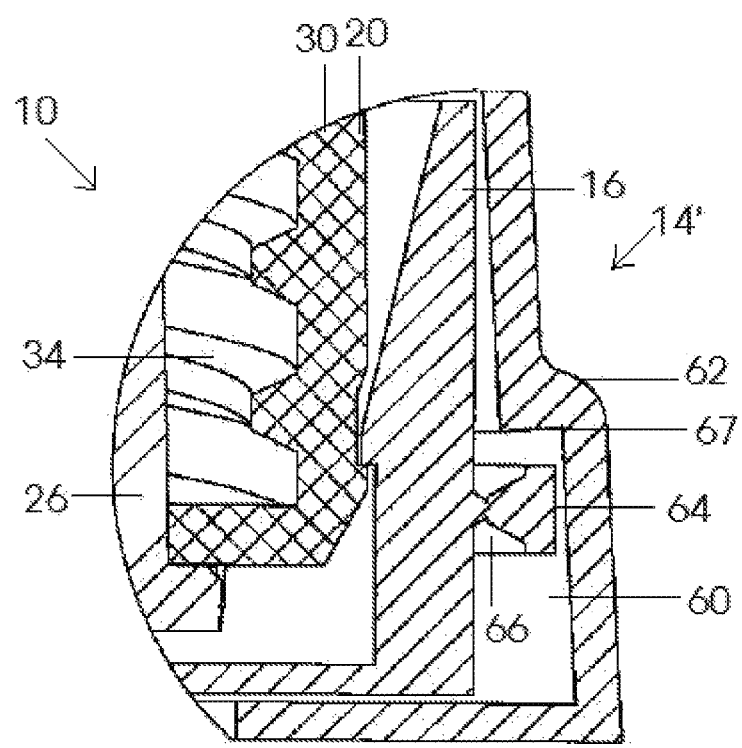
FIG. 8 is interior sectional view in cutaway taken along line 8-8 of FIG. 7, representing details of the embodiment of FIGS. 6-7.

Yet an additional feature of one or more other embodiments of the closure assembly 10 is represented in FIGS. 6 and 8 and comprises a tamper evident structure, generally indicated as 60, operative to clearly indicate an attempted or actual access to the medical connector 12 and/or the contents of a liquid reservoir or other container with which the medical connector 12 is operatively associated. More specifically, when one or more embodiments of the closure assembly 10 incorporates the tamper evident structure 60, the housing assembly 14' may include an outer cover 62 disposed in surrounding, enclosing relation to the closure sleeve 16 and the closure cap 20, when disposed within the interior of the closure sleeve 16. Further, this tamper evident structure 60 preferably, but not exclusively, comprises a tamper evident ring 64 or like structure removably connected to the exterior surface of the cap 20 by frangible type connecting structures 66. As such, the outer cover of the housing assembly 14' includes interior structural portions 67 disposed in interruptive, abutting relation and or engagement with the tamper evident ring 64 or other type tamper evident structure. Therefore, when a sufficient, outwardly directed pulling force 102 is exerted on the medical connector 12, the tamper evident ring 64 or like structure will be forced into abutting engagement with the interior structure 67 of the outer cover 62. This will result in disconnection of the ring 64 from the exterior surface of the closure sleeve 16 and a capturing of the ring 64 inside the outer cover 62. Therefore, a disconnection of the tamper evident structure or ring 64 will be indicative of an intended or actual use and/or access to the medical connector 12 and/or the contents of a fluid reservoir associated with the medical connector.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A closure assembly structured for attachment to a medical connector, said closure assembly comprising:
    a cap including a flow restricting portion, said cap structured for direct, removable attachment to the medical connector,
    a housing assembly including an access opening and a hollow interior dimensioned to receive said cap and the medical connector attached thereto,
    said cap including a sidewall comprising at least one segment movably attached to a remainder of said cap,
    said one segment being movable between an open orientation and a closed orientation relative to said flow restricting portion,
    said closed orientation comprising said one segment disposed in retaining relation with the medical connector, and
    said sidewall and said at least one segment collectively and cooperatively dimensioned with said access opening to force movement of said at least one segment from said open orientation to said closed orientation upon passage of said cap through said access opening and into said hollow interior of said housing assembly.

2. The closure assembly as recited in claim 1 wherein said closed orientation further comprises a remainder of said sidewall disposed in said retaining relation with the medical connector concurrently with said one segment.

3. The closure assembly as recited in claim 1 wherein said one segment includes an interior surface cooperatively structured with an exterior of the medical connector to define said retaining relation as a substantially mating engagement between said one segment and the medical connector.

4. The closure assembly as recited in claim 3 wherein said mating engagement comprises an at least partially threaded engagement.

5. The closure assembly as recited in claim 1 wherein said sidewall comprises a plurality of segments hingedly connected to a remainder of said cap, said plurality of segments independently and collectively movable between said open and closed orientations.

6. The closure assembly as recited in claim 5 wherein said closed orientation comprises said plurality of segments concurrently disposed in said retaining relation with the medical connector.

7. The closure assembly as recited in claim 6 wherein at least some of an interior surface is cooperatively structured with an exterior of the medical connector to define said retaining relation as a substantially mating engagement between respective ones of said plurality of segments and the medical connector.

8. The closure assembly as recited in claim 7 wherein said retaining mating engagement comprises an at least partially threaded engagement.

9. The closure assembly as recited in claim 1 wherein said open orientation comprises a movable, outwardly extended position of said one segment relative to said flow restricting portion and the medical connector connected to said cap.

10. The closure assembly as recited in 1 wherein said cap comprises a base, said one segment hingedly connected to said base and movable relative thereto between said open and closed orientations.

11. The closure assembly as recited in claim 10 wherein said one segment includes a length sufficient to extend continuously from said base to an open end of said cap disposed opposite to said base.

12. The closure assembly as recited in claim 10 wherein said open orientation comprises said one segment disposed laterally outward from said base away from the flow restricting portion and the medical connector attached to said cap.

13. The closure assembly as recited in claim 1 further comprising a retaining structure at least partially formed on an interior of said housing assembly, said retaining structure disposed in abutting, retaining engagement with an exterior of at least said one segment, when said cap is disposed within said housing assembly.

14. The closure assembly as recited in claim 13 wherein said retaining structure is disposed in removal restricting relation to said cap when in said retaining engagement.

15. The closure assembly as recited in claim 14 wherein said retaining structure is disposed out of said abutting, retaining engagement with said one segment upon a squeezing force being exerted on an exterior of said housing assembly.

16. The closure assembly as recited in claim 1 wherein said flow restricting portion comprises a plug disposed within said cap and extending outwardly from a base of said cap into a flow restricting relation within a female flow port of the medical connector.

17. A closure assembly structured to be attached in flow restricting relation to a medical connector, said closure assembly comprising:
    a housing assembly comprising a closure sleeve including an access opening,
    a cap including a base and a flow restricting portion disposed on an interior of said cap; said cap operatively disposed in removable, flow restricting attachment to the medical connector,
    said cap including a plurality of segments collectively defining a sidewall of said cap; said plurality of segments movably connected to said base,
    said plurality of segments movable between an open orientation and a closed orientation relative to said flow restricting portion and said base,
    said closed orientation comprising said plurality of segments disposed in retaining relation with the medical connector when said medical connector is disposed in said flow restricting attachment with said cap, and
    said plurality of segments collectively and cooperatively dimensioned with said access opening to force concurrent movement of said plurality of segments from said open orientation to said closed orientation, upon passage of said cap through said access opening, into said housing assembly.

18. The closure assembly as recited in claim 17 wherein each of said plurality of segments includes a length sufficient to extend continuously from said base to an open end of said cap opposite to said base.

19. The closure assembly as recited in claim 18 wherein said open orientation comprises said plurality of segments disposed laterally outward from said base away from the medical connector attached to said cap.

20. The closure assembly as recited in claim 17 wherein each of said plurality of segments include an interior surface cooperatively structured with an exterior surface of the medical connector to define said retaining relation as a substantially mating engagement between each of said plurality of segments and the medical connector.

21. The closure assembly as recited in claim 20 wherein said mating engagement comprises an at least a partially threaded engagement.

22. The closure assembly as recited in claim 17 wherein said housing further comprises a cover and said closure sleeve disposed within said cover; a tamper evident structure removably connected to an exterior of said closure sleeve; interior portions of said cover disposed in interruptive, disconnecting engagement with said tamper evident structure, upon removal of said closure sleeve, said cap and the attached medical connector, from said cover through an open end of said cover.

23. The closure assembly as recited in claim 22 wherein said tamper evident structure comprises a continuously configured ring removably connected to an exterior surface of said closure sleeve.

24. The closure assembly as recited in claim 17 wherein said flow restricting portion comprises a plug disposed within said cap and extending outwardly from said base thereof into a flow stopping relation to a female flow port of the medical connector.

25. A closure assembly structured to be attached in flow restricting relation to a medical connector, said closure assembly comprising:
   a housing assembly comprising a closure sleeve including an access opening,
   a cap including a base and a flow restricting portion disposed on an interior of said cap; said cap operatively disposed in removable, flow restricting attachment to the medical connector,
   said cap including a plurality of segments collectively defining a sidewall of said cap; said plurality of segments movably connected to said base,
   said plurality of segments movable between an open orientation and a closed orientation relative to said flow restricting portion and said base,
   said closed orientation comprising said plurality of segments disposed in retaining relation with the medical connector when said medical connector is disposed in said flow restricting attachment with said cap,
   a retaining structure at least partially formed on an interior of said closure sleeve, and
   said retaining structure disposed in abutting,
   retaining engagement with an exterior of at least some of said plurality of segments, when said cap and the medical connector are disposed within said housing assembly.

26. The closure assembly as recited in claim 25 wherein said retaining structure is disposed in removal restricting relation to said cap when in said retaining engagement.

27. A closure assembly structured to be attached in flow restricting relation to a medical connector, said closure assembly comprising:
   a housing assembly comprising a closure sleeve including an access opening,
   a cap including a base and a flow restricting portion disposed on an interior of said cap; said cap operatively disposed in removable, flow restricting attachment to the medical connector,
   said cap including a plurality of segments collectively defining a sidewall of said cap; said plurality of segments movably connected to said base,
   said plurality of segments movable between an open orientation and a closed orientation relative to said flow restricting portion and said base,
   said closed orientation comprising said plurality of segments disposed in retaining relation with the medical connector when said medical connector is disposed in said flow restricting attachment with said cap, and
   said cap and the medical connector attached thereto are freely rotatable, in opposite directions, within said housing assembly.

28. The closure assembly as recited in claim 27 wherein said cap is at least temporarily disposed in fixed relation to said closure sleeve, upon substantially opposing, squeezing forces being concurrently exerted on an exterior of said closure sleeve; the medical connector being rotationally removed from the cap concurrent to said fixed relation between said closure sleeve and said cap.

* * * * *